United States Patent
Schatz et al.

(10) Patent No.: US 10,519,408 B2
(45) Date of Patent: Dec. 31, 2019

(54) PROCESS FOR OPTIMIZING THE OPERATION OF A PLUG-FLOW FERMENTER FOR THE ANAEROBIC FERMENTATION OF ORGANIC WASTES

(71) Applicant: HITACHI ZOSEN INOVA AG, Zürich (CH)

(72) Inventors: Adrian Schatz, Niederwangen (CH); Marc Eugster, Dállikon (CH)

(73) Assignee: HITACHI ZOSEN INOVA AG, Zurich (CH)

( * ) Notice: Subject to any disclaimer, the term of this patent is extended or adjusted under 35 U.S.C. 154(b) by 0 days.

(21) Appl. No.: 16/116,454

(22) Filed: Aug. 29, 2018

(65) Prior Publication Data

US 2019/0062682 A1 Feb. 28, 2019

(30) Foreign Application Priority Data

Aug. 29, 2017 (EP) .................................. 17188374

(51) Int. Cl.
| | |
|---|---|
| *C12M 1/02* | (2006.01) |
| *C02F 3/28* | (2006.01) |
| *C12M 1/06* | (2006.01) |
| *C12M 1/34* | (2006.01) |
| *C12M 1/107* | (2006.01) |
| *C12M 1/00* | (2006.01) |

(Continued)

(52) U.S. Cl.
CPC .............. *C12M 1/02* (2013.01); *C12M 21/04* (2013.01); *C12M 23/02* (2013.01); *C12M 27/06* (2013.01); *C12M 29/02* (2013.01); *C12M 41/12* (2013.01); *C12M 41/42* (2013.01); *C12M 41/44* (2013.01); *C12M 41/48* (2013.01); *C02F 3/28* (2013.01); *C02F 2209/00* (2013.01); *C12M 21/16* (2013.01)

(58) Field of Classification Search
CPC ........ C12M 1/02; C12M 23/02; C12M 41/48; C12M 41/44; C12M 41/42; C12M 29/02; C12M 21/04; C12M 27/06; C12M 41/12; C12M 21/16; C02F 3/28; C02F 11/04; C02F 2209/00
USPC ............................... 210/603, 614; 435/293.1
See application file for complete search history.

(56) References Cited

U.S. PATENT DOCUMENTS

2008/0032375 A1* 2/2008 Hartmann ................. B01F 7/04
435/170

FOREIGN PATENT DOCUMENTS

| DE | 102005041798 A1 | 3/2007 |
|---|---|---|
| DE | 102014116239 A1 | 5/2016 |

(Continued)

OTHER PUBLICATIONS

Machine-generated English translation of WO 2006//079228, generated on May 16, 2019.*

(Continued)

*Primary Examiner* — Fred Prince
(74) *Attorney, Agent, or Firm* — Oliff PLC

(57) ABSTRACT

A process for optimizing the operation of a plug-flow fermenter for the anaerobic fermentation of organic wastes, wherein the plug-flow fermenter comprises a horizontally oriented fermenter tank and a stirrer, which stirrer comprises a stirrer shaft which traverses the interior of the fermenter tank in an axial manner and multiple paddles which are arranged on the stirrer shaft and protrude radially and also a drive, and the fermentation material is moved in the fermenter tank by means of the stirrer.

12 Claims, 2 Drawing Sheets

Figure 1:
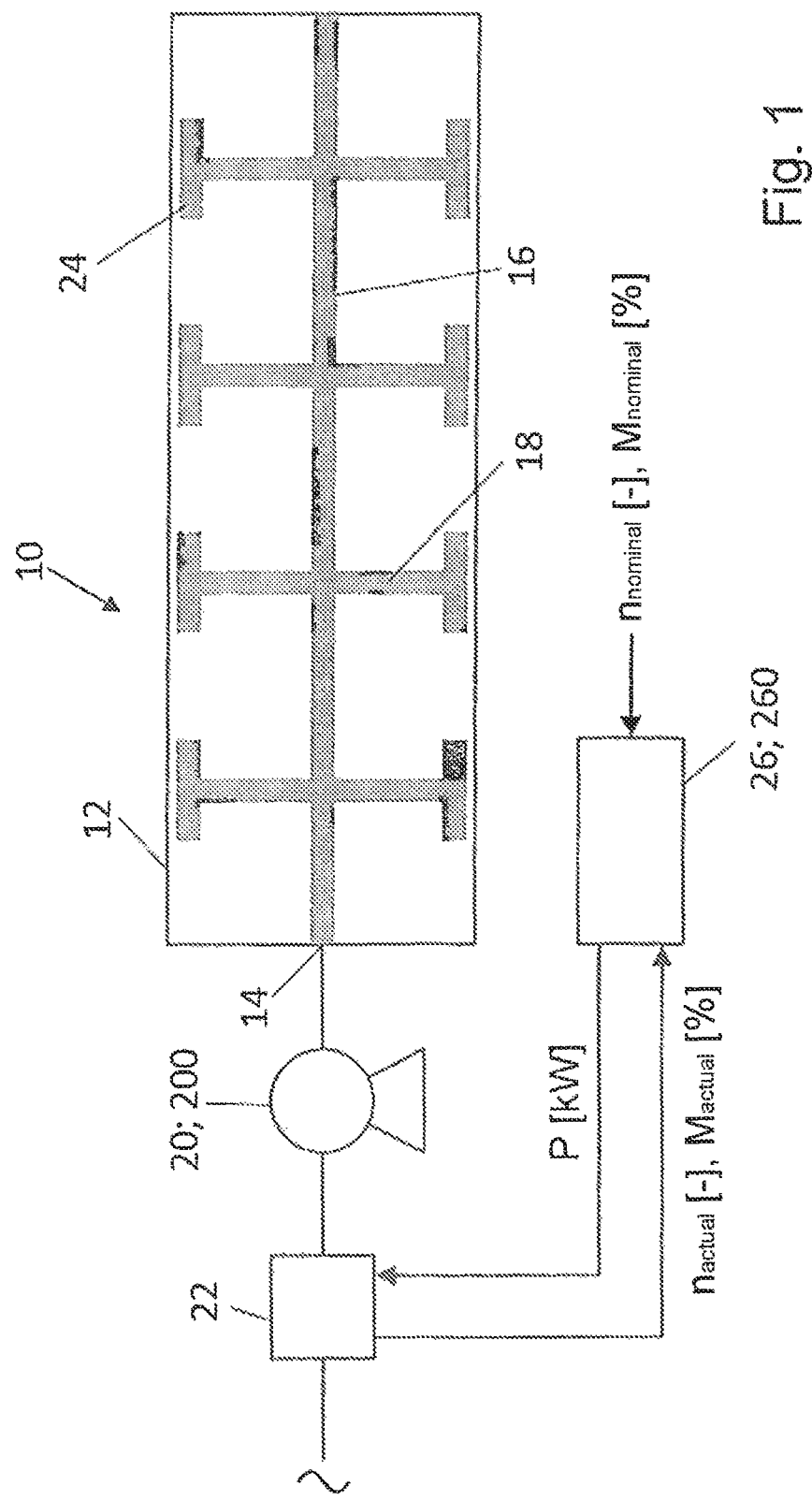

(51) Int. Cl.
*C12M 1/36* (2006.01)
*C12M 1/16* (2006.01)

(56) References Cited

FOREIGN PATENT DOCUMENTS

| RU | 102617 U1 | 3/2011 |
| WO | 2005/113469 A1 | 12/2005 |
| WO | 2006/079228 A1 | 8/2006 |
| WO | 2011/121024 A1 | 10/2011 |
| WO | 2016/071454 A1 | 5/2016 |

OTHER PUBLICATIONS

Machine-generated English translation of WO 2016//071454, generated on May 16, 2019.*
Feb. 26, 2018 Search Report issued in European Patent Application No. 17188374.
Aug. 13, 2019 Office Action issued in Russian Patent Application No. 2018130990.

* cited by examiner

PROCESS FOR OPTIMIZING THE OPERATION OF A PLUG-FLOW FERMENTER FOR THE ANAEROBIC FERMENTATION OF ORGANIC WASTES

The invention relates to a process for optimizing the operation of a plug-flow fermenter for the anaerobic fermentation of organic wastes and to a correspondingly designed plug-flow fermenter.

Processes for the anaerobic fermentation of organic wastes are known to a person skilled in the art and have gained in importance especially in recent years, since they, firstly, allow an ecological waste management, but, secondly, are also of interest economically because significant amounts of biogas can be generated thereby.

Among the known anaerobic fermentation processes, a fundamental distinction can be made between liquid or wet fermentation processes and the so-called dry fermentation processes. Whereas wet fermentation processes are usually carried out in one or more vertically oriented fermenters, in the case of the so-called dry fermentation processes, the fermentation material is generally fermented in a horizontally oriented fermenter.

The dry-substance portion of the fermentation material is, in this connection, substantially higher than in the case of wet fermentation processes; nevertheless, the fermentation material has a considerable liquid portion even in the dry fermentation.

Dry fermentation processes can be carried out especially in a plug-flow fermenter, as are known for instance from EP-A-0476217. Such fermenters generally comprise an elongated, horizontal fermenter tank having a fermenter inlet provided at one end and a fermenter outlet arranged at the opposite end.

The organic wastes to be fermented are inputted in comminuted form on the inlet side and inoculated with already fermented material and/or press water from the fermentation-residue processing step. As a result, the material to be fermented is enriched with methane bacteria. In the fermenter tank, the wastes are then degraded under controlled mixing to form biogas and subsequently, i.e., after leaving through the fermenter outlet, fed to a fermentation-residue processing step and then to an aerobic rotting step.

The stirrer of such plug-flow fermenters must, firstly, ensure that the fermentation material is thoroughly mixed with methane bacteria for the purposes of a fermentation that is as optimal as possible. Moreover, the aim is to ensure a good degassing as a result of the mixing or of the continuous surface renewal which arises.

Furthermore, the stirrer must ensure that heavier solids components of the fermentation material which can sediment at the bottom of the fermenter tank can be transported into the upper layers and that even these components of the fermentation material are thus transported through the fermenter tank and leave it at a given time.

The goal of reducing the residence time of the fermentation material in the fermenter and of thus increasing the possible throughput is dealt with by, for instance, WO 2005/113469, according to which fresh material or fermentation material can be fed through multiple inlet openings and/or fermentation material can be removed through multiple fermentation-material discharge openings.

Especially in the case of plug-flow fermenters, there is frequently the problem that portions of the fermentation material can solidify on the stirrer shaft and that they remain adherent thereon. The associated weight gain automatically leads to a higher load on the stirrer shaft and thus to the deflection thereof. This in turn can lead to the paddles arranged on the stirrer shaft and blades arranged on the radially outer end of the paddles rubbing on the wall of the fermenter tank, the result of this being that the torque at the shaft further increases and, moreover, wear and tear appear on the fermenter tank wall. Furthermore, despite prior comminution of the biogenic wastes, elongated solids such as ropes, wires or loop-type green wastes can get into the fermenter again and again, and wrap around the stirrer shaft during operation. These effects can lead to an impairment of fermenter operation and, in the worst case, to malfunction thereof.

Proceeding from the above-described problems, EP-A-1841853 proposes a process for operating a plug-flow fermenter, in which a) the stirrer is rotated in a direction where a plowing action is achieved with shares arranged in a V-shaped manner, b) the stirrer is rotated in an opposite direction where the blades achieve a conveying action, and c) the stirrer stands still.

However, the process described in EP-A-1841853 accommodates the inhomogeneity of the fermentation material only to a limited extent. This can lead to suboptimal fermentation and degassing of the fermentation material in the fermenter tank because of insufficient mixing or an excessively short residence time. On the other hand, the energy expenditure of the stirrer is greater than required for efficient mixing and conveyance, and this is reflected in a suboptimal energy balance.

Against this background, it is an object of the invention to provide a process for optimizing the operation of a plug-flow fermenter for the anaerobic fermentation of organic wastes. In particular, the aim is to ensure an optimal fermentation and degassing with as low an energy expenditure as possible.

The object is achieved by the process according to the invention as claimed in claim 1. Preferred embodiments of the invention are defined in the dependent claims.

According to claim 1, the plug-flow fermenter, the operation of which is to be optimized, comprises a horizontally oriented fermenter tank and a stirrer. The stirrer, on its part, comprises a stirrer shaft which traverses the interior of the fermenter tank in an axial manner and multiple paddles which are arranged on the stirrer shaft and protrude radially and also a drive. The fermentation material is moved in the fermenter tank by means of the stirrer. As a result, the fermentation material is, firstly, mixed, and, secondly, the movement generally also supports the conveyance of the fermentation material from the fermenter inlet in the direction of the fermenter outlet.

The operation optimization that is striven for is, then, obtained according to the invention in that a) at least one parameter characteristic of the particular operating state of the plug-flow fermenter is measured, b) the particular measurement value $A_{actual}$ obtained in a) is compared with a predefined nominal value $A_{nominal}$, and c) depending on the deviation of the measurement value $A_{actual}$ from the nominal value $A_{nominal}$, the rotational speed of the stirrer shaft, the rotational direction of the stirrer shaft and/or the dry-substance portion of the fermentation material is adjusted.

According to the invention, it is therefore possible to check, via the determination of the particular parameter that takes place in step a) and b) and via the comparison with a corresponding nominal value, whether there is an "overload" or an "underload" of the system in the case of the present rotational speed and rotational direction of the stirrer shaft. If there is such an "overload" or "underload", it can be specifically counteracted via adjustment of the rotational speed and/or the rotational direction. Alternatively or additionally, the dry-substance portion of the fermentation material can also be adjusted in order to optimize the throughput thereof. This ultimately allows an optimal treatment of the fermentation material, with the energy expenditure expended for this purpose being kept to a minimum at the same time.

The process or the plug-flow fermenter of the present invention is designed for dry fermentation. Therefore, the invention fundamentally differs from the wet fermentation processes described at the start and the vertical systems intended for this purpose, for which reference is made by way of example to DE 10 2014 116 239 A1 and to WO 2011/121024 A1 belonging to the same patent family. Thus, according to the technology described in WO 2011/121024 A1, two stirrers having propellers are arranged in a vessel, wherein the propellers are made to rotate and mostly generate horizontal flows of the vessel content. In line with the wet fermentation technology which is fundamentally different in comparison with the present invention and in line with the different object, namely that of maximizing the converted amount of fermentation substrate and the residence time required therefor and of forming a larger effective mixing zone in the vessel volume (which tends to have many dead regions), the device overall, and in particular the stirrer, according to WO 2011/121024 A1 is also of a completely different design than that of the present invention. For instance, neither is there a stirrer shaft which traverses the interior of the vessel in an axial manner, nor do the stirrers according to WO 2011/121024 A1 have paddles which protrude radially.

As mentioned, it is possible in step c) of the process according to the invention to adjust the dry-substance portion of the fermentation material and to thus ultimately adapt the conveyability thereof. Generally, this is done via the adjustment of the amount of wetting agent introduced into the fermenter tank and thus added to the fermentation material. However, it is also conceivable to adjust the dry-substance portion via the amount of the fermentation material introduced into the fermenter tank.

Specifically, the dry-substance portion of the fermentation material is preferably within the range between 5 to 99%, more preferably between 15 to 40%, and thus distinctly above the dry-substance portion present in wet fermentation systems.

In the context of the present invention, the term "waste" is used for the material which is present in the feed and is to be fermented, whereas "fermentation material" refers to the waste-based material which is present in the fermenter tank, has been inoculated and is being fermented.

The wastes and the fermentation material in the context of the present invention are in particular a relatively inhomogeneous material, and what is meant thereby is that the dry-substance portion comprises solids particles or solids constituents of differing size and shape. In particular, solids constituents of a relatively large volume may be present therein. Typically, the organic wastes are mixtures of wastes such as domestic, garden, agricultural, industrial and green wastes, food leftovers and animal excrements such as solid manure. The advantages obtained according to the invention make a particular difference especially in the case of such inhomogeneous materials, since the rotational speed and rotational direction of the stirrer shaft that are optimal for the system as well as the optimal dry-substance portion may be subject to constant fluctuations, which can be compensated for in accordance with the invention.

The term "nominal value", as used in the context of the present invention, includes in particular a nominal value range. In other words, there is, according to the invention, then a deviation of the measurement value $A_{actual}$ from the nominal value $A_{nominal}$ when the measurement value is higher than the upper limit of the nominal value range or lower than the lower limit of the nominal value range.

Specifically, no nominal load curve, as taught by DE 10 2014 116 239 A1 for instance, is deposited according to the invention. In the process of the present invention, the deposition of a nominal load curve would only make sense technically to a limited extent, especially also in view of the inhomogeneity of the fermentation material.

As mentioned, the rotational speed of the stirrer shaft, the rotational direction of the stirrer shaft and/or the dry-substance portion of the fermentation material is adjusted in step c) depending on the deviation of the measurement value $A_{actual}$ from the nominal value $A_{nominal}$. According to a preferred embodiment, the rotational speed and/or the rotational direction of the stirrer shaft and/or the dry-substance portion of the fermentation material is, in this connection, not only adjusted one time, but also regulated. In other words, the impact of the change in the rotational speed and/or the rotational direction and/or in the dry-substance portion on the deviation of the measurement value $A_{actual}$ from the nominal value $A_{nominal}$ is continuously monitored and, on that basis, the rotational speed, the rotational direction and/or the dry-substance portion are further adapted or retained, with the result that there is a closed sequence of action.

The present invention therefore fundamentally differs from the process described in WO 2006/079228 A1 for operating a plug-flow fermenter, according to which predefined steps a) to c) are carried out, wherein a stirrer rotates in a predefined (first) direction in a step a) in order to achieve a plowing action, in a reverse (second) direction in a step b) in order to achieve a conveying action, and stands still in a step c). However, WO 2006/079228 A1 does not disclose adjusting the rotational direction of the stirrer depending on a parameter characteristic of the operating state of the fermenter or the deviation thereof from a nominal value. Apart from that, WO 2006/079228 A1 does not teach or disclose adjusting the rotational speed of the stirrer shaft and/or the dry-substance portion of the fermentation material.

Preferably, the range within which the rotational speed of the stirrer shaft is adjusted is between 0 and 10, preferably between 0 and 1, particularly preferably between 0.2 to 0.6 revolutions per minute. The rotational speed of the stirrer shaft therefore differs very substantially from the rotational speed of a propeller, as can be used for instance in a wet fermentation process and as is present for instance according to the technology described in DE 10 2014 116 239 A1 and WO 2011/121024 A1 and is used with rotational speeds in the order of magnitude of from 30 to 180 revolutions per minute.

The paddles arranged on the stirrer shaft and the blades optionally arranged on the radially outer end of the paddies primarily serve to mix the fermentation material for an optimal fermentation. In this connection, it is conceivable to design the paddles and in particular the blades arranged thereon in a symmetrical manner, with the result that no active conveyance component toward the fermenter outlet is imparted to the fermentation material by the paddles and blades. In this connection, it is especially conceivable to design the blades asymmetrically with respect to the rotational direction, with the result that there is a radial conveyance action on the fermentation material in the case of a first rotational direction and a plowing action in the case of a second rotational direction. In this embodiment, the propulsion of the fermentation material arises primarily as a result of the advancement of fermentation material through the fermenter inlet, with the conveyance being supported by the fermentation material movement generated by means of the stirrer shaft. However, it is also conceivable to design the blades such that an active, axial conveyance component in the direction of the fermenter outlet is imparted to the fermentation material.

As parameter characteristic of the operating state, it is possible according to the invention to select in particular at least one of the following parameters A1) to A4):

A1: the torque and/or the power of the drive;
A2: at least one temperature present in the fermenter tank;
A3: the flow rate and/or the composition of the fermentation material at at least one point in the fermenter tank; and/or
A4: the composition and/or the amount of the gas generated by the anaerobic fermentation.

In this connection, according to a particularly preferred embodiment, the torque and/or the power of the drive, i.e., parameter A1, is determined. In this regard, it is conceivable for instance for the power of the drive to be ascertained on the control side via the product of the current and the voltage. Furthermore, it is conceivable for the torque to be derived from the power of the drive. According to a particularly preferred embodiment, the drive is present in the form of a motor, specifically an asynchronous motor, to which a frequency converter has been assigned; in this case, it is preferred that the torque in percent at the frequency converter is ascertained.

Proceeding from the measurement value $A1_{actual}$, as obtained in step a), of the torque and/or the power of the drive, the rotational speed is reduced according to a further preferred embodiment of the process according to the invention if the measurement value $A1_{actual}$, as obtained in step a), of the torque or the power is higher than a predefined maximum value $A1_{max}$.

In this case, the torque or the power is then measured at reduced rotational speed.

Lastly, if the value $A1_{actual,red}$ measured at reduced rotational speed is still higher than $A1_{max}$, the torque or the power is further reduced, whereupon the measurement of the torque or the power at further reduced rotational speed and the subsequently performed further reduction of the rotational speed are repeated at least once, preferably multiple times, as desired and/or the rotational direction of the stirrer shaft changed.

Thus, in the event of the system being overloaded, it is relieved by reducing the rotational speed and/or by changing or reversing the rotational direction, the indicator used for a system overload being the fact that the torque or the power of the drive exceeds a predefined nominal value. The concept of this preferred embodiment is thus diametrically opposed to that of WO 2011/121024 A1, according to which, in the event of excessively high viscosity, the rotational speed of the stirrers is increased or the power input is increased by switching on further stirrers in order to prevent a collapse of the common mixing zone into individual caverns.

Preferably, the rotational speed in the particular step is reduced only to a slight extent, with the result that the difference arising owing to the reduction in rotational speed is within a range from 0.001 to 0.1 revolutions per minute, preferably approximately 0.05 revolutions per minute. This can ensure that, even with reduced rotational speed, it is still sufficiently high for ensuring sufficient mixing of the fermentation material.

If the rotational direction of the stirrer shaft is changed, it may be preferable, subsequent to this change, to change the rotational direction of the stirrer shaft after a period t, the result being that the original rotational direction is obtained. This is especially the case when the paddles and/or blades possibly arranged thereon are arranged asymmetrically with respect to the rotational direction, with the result that there is a radial conveyance action on the fermentation material in the case of a first rotational direction and a plowing action in the case of a second rotational direction, by means of which a loosening of accumulating fermentation material can be brought about, whereupon the fermentation material can—after re-reversal of rotational direction—be conveyed more easily.

As an alternative to the above-described process in which a system overload is established, it is also conceivable for the measurement value $A1_{actual}$, as obtained in step a), of the torque or the power to be lower than a predefined minimum value $A1_{min}$, this indicating an "underload" of the system. In this case, the rotational speed of the stirrer shaft is preferably reduced and the system is thus shifted to an energy-saving mode, in which it is nevertheless possible to ensure that the mixing and the conveyance of the fermentation material is sufficiently high.

The reduced rotational speed or the energy-saving mode is maintained so long as the measurement value $A1_{actual}$ is lower than $A1_{min}$. If it is established that the measurement value $A1_{actual}$ exceeds the minimum value $A1_{min}$, the rotational speed is raised, with the result that $A1_{actual}$ lies within the range defined by the limits $A1_{min}$ and $A1_{max}$.

Besides the above-described process, the present invention also provides, according to a further aspect, a plug-flow fermenter equipped for the process.

Thus, the plug-flow fermenter comprises not only the above-described fermenter tank and the stirrer, but also at least one measurement mechanism for the determination of at least one parameter characteristic of the particular operating state of the plug-flow fermenter as well as adjustment means designed to adjust the rotational speed and/or the rotational direction of the stirrer shaft on the basis of the measurement value obtained or the deviation of the measurement value from a predefined nominal value.

Preferably, the adjustment means are present in the form of or as part of a regulation unit designed to regulate the rotational speed and/or the rotational direction of the stirrer shaft on the basis of the measurement value obtained or the deviation of the measurement value from the nominal value.

Furthermore, it is preferred that the drive is a motor, more particularly an asynchronous motor, to which a frequency converter has been assigned.

Figure 2:
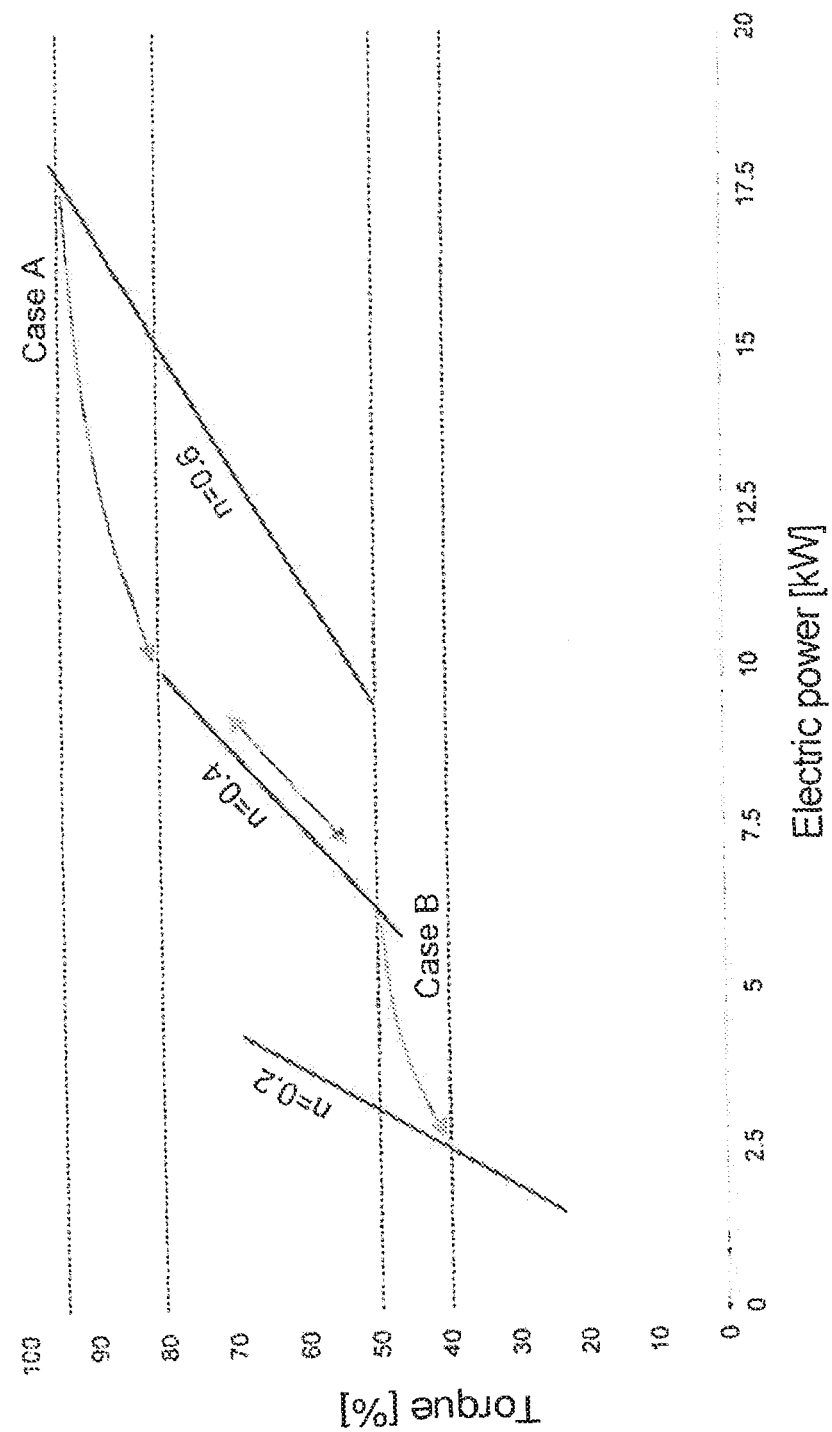

The invention will be further illustrated on the basis of the figures, where:

FIG. 1 shows a diagram of a regulation system in accordance with the process of the present invention; and FIG. 2 shows a graph in which torque values (in % at the frequency converter) have been plotted against the drive power that is present in each case, and in which, moreover, nominal values at different rotational speeds of the stirrer shaft have been defined.

According to FIG. 1, the process according to the invention is carried out by using a plug-flow fermenter 10 which comprises a horizontally oriented fermenter tank 12 and a stirrer 14.

The stirrer 14 comprises a stirrer shaft 16 which traverses the interior of the fermenter tank 12 in an axial manner and multiple paddles 18 which are arranged on the stirrer shaft and protrude radially and also a drive 20 which is, in this specific case, present in the form of an asynchronous motor 200, to which a frequency converter 22 has been assigned. Apart from that, arranged on the radially outer end of the paddles 18 are blades 24 which are designed to mix the fermentation material and, as a result, to support the conveyance of the fermentation material toward the fermenter outlet.

In the exemplary embodiment shown in FIG. 1, the torque $M_{actual}$ [%] at the frequency converter 22 is measured in a step a) at a present rotational speed $n_{actual}$ [rpm] of the stirrer shaft 16.

The measurement value obtained is compared with a nominal value $M_{nominal}$ [%], specifically a nominal value range, in a step b).

If the result of this comparison is that the determined value of the torque or the power is above a maximum value of the nominal value range (case A), this for instance possibly being the case in the event of a relatively high dry-substance content of the fermentation material, the system is relieved by giving the frequency converter 22 the signal, via adjustment means 26 in the form of a regulation unit 260, to reduce the rotational speed in step c) to the value $n_{nominal,new}$.

Subsequently, the torque to be applied for the reduced rotational speed $n_{nominal,new}$ of the stirrer shaft 16 is determined and compared with the maximum value $M_{max}$.

If the torque is still too high, this indicates congestion of the fermentation material. This can be countered by repeating multiple times the reduction of the rotational speed with the subsequent measurement of the torque to be applied at reduced rotational speed and with the comparison of the torque with the maximum value until the torque is below the maximum value. Alternatively, the rotational direction of the stirrer shaft can also be changed. Depending on the design of the paddles and blades possibly arranged thereon, a plowing action can therefore be obtained in order to disperse the congestion of the fermentation material. Moreover, if the excessively high torque is inter alia a result of fermentation material constituents congested on the paddles, changing the rotational direction can achieve a loosening and ultimately a removal of said constituents from the paddles.

By contrast, if it is established in step b) that the torque is below a minimum value of the nominal value range (case B), this indicates an "underload" of the system. This is responded to by minimizing the rotational speed to a minimum rotational speed or completely switching it off and thus switching the drive to an energy-saving mode.

Alternatively or additionally, it is conceivable, on the basis for instance of the composition of the fermentation material at at least one point in the fermenter tank and/or after exit from the fermenter tank, to draw conclusions as to whether the mixing in the fermenter tank (at reduced rotational speed) is sufficient.

The different scenarios are represented in the graph according to FIG. 2, where a nominal value range between 50 and 80% and a minimum rotational speed of 0.2 revolutions per minute (rpm) have been predefined for the torque at the frequency converter.

If the result of the determination of the torque is that it, at a rotational speed of the stirrer shaft of 0.6 rpm, is 95% and thus too high, the rotational speed is reduced, the rotational speed being reduced to 0.4 rpm in the specific example, whereupon the torque is redetermined and compared with the nominal value or the maximum value of the nominal value range.

By contrast, if, at a present rotational speed of 0.4 rpm, a drive power is ascertained which is below a predefined minimum value, in this specific case below 6 kW, the rotational speed is minimized and the system is thus switched to an energy-saving mode.

In the example shown in the graph, the rotational speed is successively reduced from the mentioned 0.4 rpm to 0.2 rpm.

LIST OF REFERENCE SIGNS

10 Plug-flow fermenter
12 Fermenter tank
14 Stirrer
16 Stirrer shaft
18 Paddles
20; 200 Drive; asynchronous motor
22 Frequency converter
24 Blades
26; 260 Adjustment means; regulation unit

The invention claimed is:

1. A process for optimizing the operation of a plug-flow fermenter for an anaerobic fermentation of organic wastes, wherein the plug-flow fermenter comprises a horizontally oriented fermenter tank and a stirrer, which stirrer comprises a stirrer shaft which traverses the interior of the fermenter tank in an axial manner and multiple paddles which are arranged on the stirrer shaft and protrude radially and also a drive, and fermentation material is moved in the fermenter tank by means of the stirrer, wherein
  a) at least one parameter characteristic of a particular operating state of the plug-flow fermenter is measured,
  b) a particular measurement value $A_{actual}$ obtained in a) is compared with a predefined nominal value $A_{nominal}$, and
  c) depending on a deviation of the measurement value $A_{actual}$ from the nominal value $A_{nominal}$, a rotational speed of the stirrer shaft, a rotational direction of the stirrer shaft and/or a dry-substance portion of the fermentation material is adjusted.

2. The process as claimed in claim 1, wherein the adjustment of the dry-substance portion of the fermentation material is done via an amount of wetting agent introduced into the fermenter tank.

3. The process as claimed in claim 1, wherein the rotational speed of the stirrer shaft, the rotational direction of the stirrer shaft and/or the dry-substance portion of the fermentation material is regulated in step c) depending on the deviation of the measurement value $A_{actual}$ from the nominal value $A_{nominal}$.

4. The process as claimed in claim 1, wherein a range within which the rotational speed of the stirrer shaft is adjusted is between 0 and 10 revolutions per minute.

5. The process as claimed in claim 1, wherein the dry-substance portion of the fermentation material is within a range between 5 to 99%.

6. The process as claimed in claim 1, wherein at least one of the following parameters A1) to A4) is measured in step a):
  A1: the torque and/or the power of the drive;
  A2: at least one temperature present in the fermenter tank;
  A3: the flow rate and/or the composition of the fermentation material at at least one point in the fermenter tank; and/or
  A4: the composition and/or the amount of gas generated by the anaerobic fermentation.

7. The process as claimed in claim 6, wherein parameter A1 is measured in step a) and in the following order if the measurement value $A1_{actual}$, as obtained in step a), of the torque or the power is higher than a predefined maximum value $A1_{max}$, the rotational speed is reduced, the torque or the power is measured at reduced rotational speed and if the value $A1_{actual,red}$, measured at reduced rotational speed, is still higher than $A1_{max}$, the torque or the power is further reduced, whereupon the measurement of the torque or the power at further reduced rotational speed and the subsequently performed further reduction of the rotational speed are repeated at least once, or multiple times, as desired and/or the rotational direction of the stirrer shaft is changed.

8. The process as claimed in claim 7, wherein, subsequent to the change in the rotational direction of the stirrer shaft, the rotational direction is changed after a period t.

9. The process as claimed in claim 6, wherein, if the measurement value $A1_{actual}$, as obtained in step a), of the torque or the power is lower than a predefined minimum value $A1_{min}$, the rotational speed is reduced and the reduced rotational speed is maintained so long as the measurement value $A1_{actual}$ is lower than $A1_{min}$.

10. A plug-flow fermenter for an anaerobic fermentation of organic wastes, wherein the plug-flow fermenter comprises a horizontally oriented fermenter tank and a stirrer, which stirrer comprises a stirrer shaft which traverses the interior of the fermenter tank and multiple paddles which are arranged on the stirrer shaft and protrude radially and also a drive and which stirrer is suited to moving fermentation material in the fermenter tank, wherein the plug-flow fermenter additionally comprises at least one measurement mechanism for the determination of at least one parameter characteristic of a particular operating state of the plug-flow fermenter as well as a regulator designed to adjust a rotational speed of the stirrer shaft, a rotational direction of the stirrer shaft and/or a dry-substance portion of the fermentation material on the basis of the measurement value obtained or a deviation of the measurement value from a predefined nominal value.

11. The plug-flow fermenter as claimed in claim 10, wherein the regulator is present in the form of or as part of a regulation unit designed to regulate the rotational speed of the stirrer shaft, the rotational direction of the stirrer shaft and/or the dry-substance portion of the fermentation material on the basis of the measurement value obtained or the deviation of the measurement value from the nominal value.

12. The plug-flow fermenter as claimed in claim 10, wherein the drive is a motor, more particularly an asynchronous motor, to which a frequency converter has been assigned.

* * * * *